United States Patent [19]

Kane

[11] Patent Number: 4,646,755

[45] Date of Patent: Mar. 3, 1987

[54] INTRODUCER TOOL FOR ENDOCARDIAL SCREW-IN LEAD

[75] Inventor: Lawrence M. Kane, Roseville, Minn.

[73] Assignee: Daig Corporation, Minnetonka, Minn.

[21] Appl. No.: 789,941

[22] Filed: Oct. 21, 1985

[51] Int. Cl.⁴ ............................................... A61N 1/05
[52] U.S. Cl. .................................. 128/785; 128/419 P
[58] Field of Search ................................. 128/784–786, 128/419 P, 642

[56] References Cited

U.S. PATENT DOCUMENTS

| | | | |
|---|---|---|---|
| 4,103,019 | 8/1978 | Harris | 128/785 |
| 4,209,019 | 6/1980 | Dutcher | 128/784 |
| 4,570,642 | 2/1986 | Kane et al. | 128/785 |

Primary Examiner—Lee S. Cohen
Attorney, Agent, or Firm—Herman H. Bains; Malcolm L. Moore; Conrad A. Hansen

[57] ABSTRACT

An introducer tool for a screw-in endocardial lead includes a plunger housing which is connected to the connector of the endocardial lead. The plunger housing is shiftable in a locking tube between retracted and advanced positions. A stylet is insertable through the plunger housing and through the lumen of the lead for shifting the helix assembly of the lead from a retracted to an advanced position. Clamping elements on the plunger housing engage the stylet to clamp the latter against movement when the plunger housing is in the advanced position. The lead may then be rotated relative to the introducer tool about the stylet to fix the helix assembly into the endocardium.

8 Claims, 14 Drawing Figures

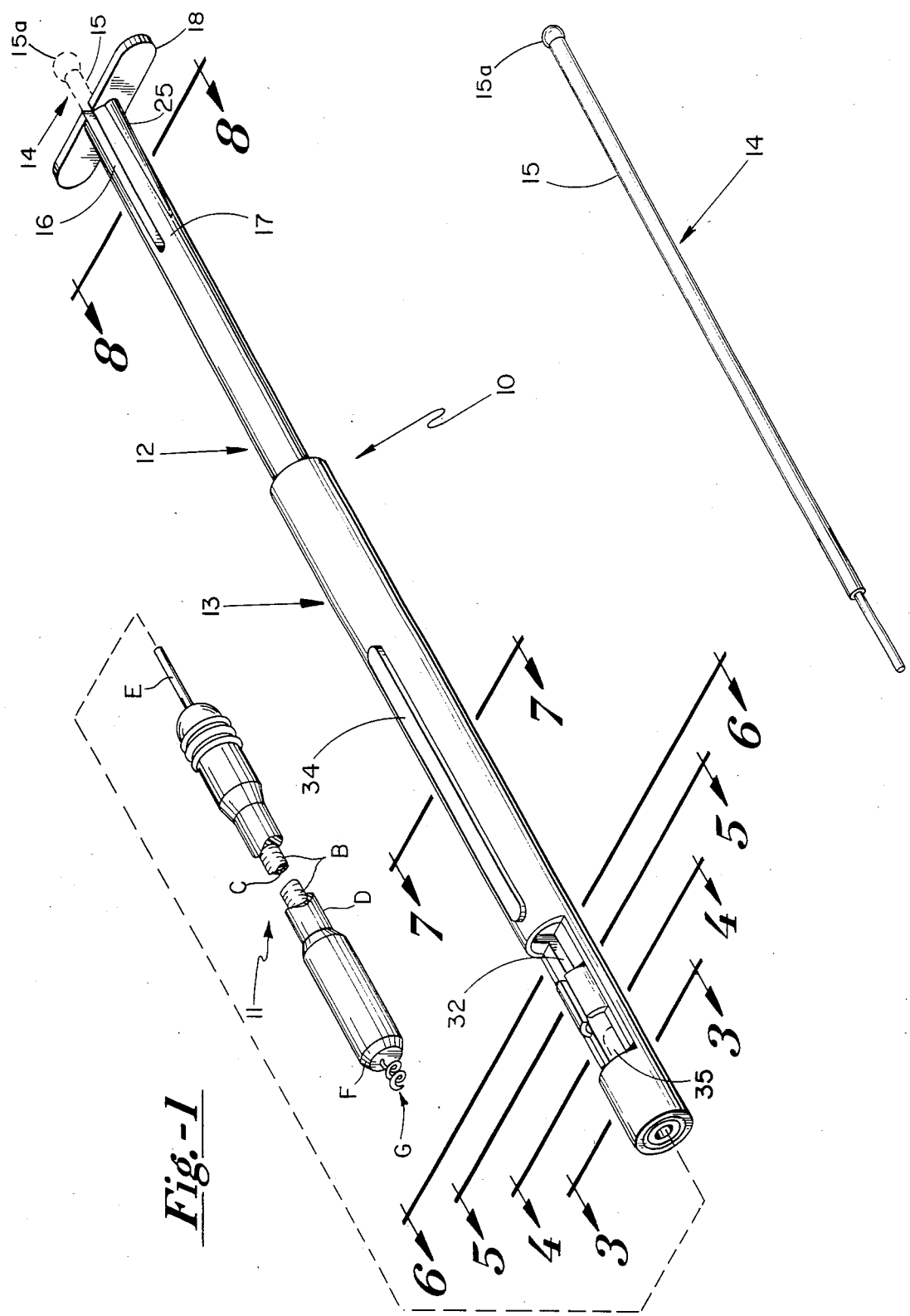

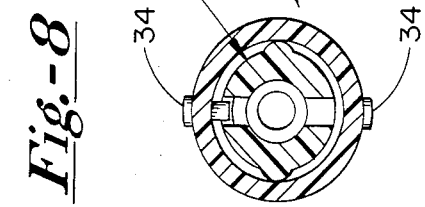
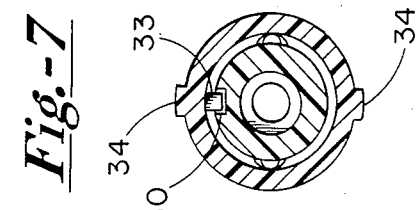
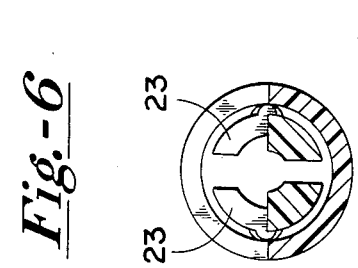
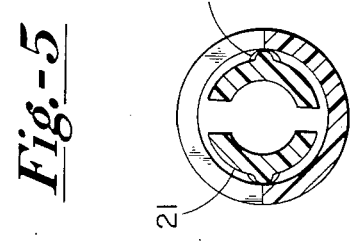
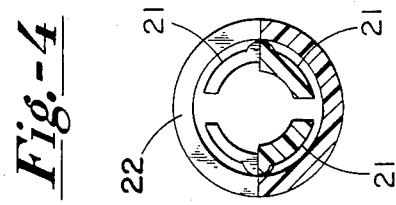
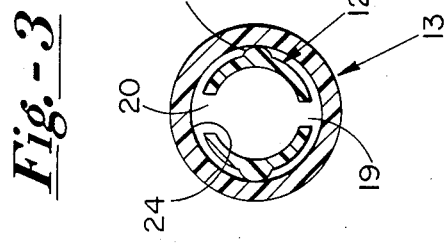
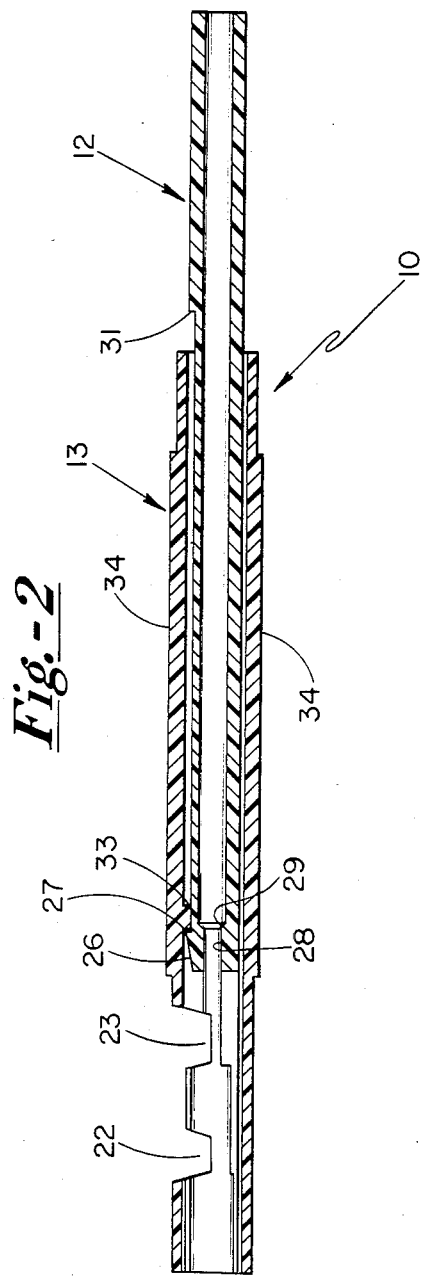

INTRODUCER TOOL FOR ENDOCARDIAL SCREW-IN LEAD

BACKGROUND OF THE INVENTION

This invention relates to an improved introducer tool for use with an endocardial lead having a helical fixation element.

Endocardial leads having a helical fixation element have long been accepted as a means for achieving positive fixation in atrial and ventricular pacing applications. An endocardial screw-in lead is disclosed in the co-pending application, entitled ENDOCARDIAL EXTENDABLE SCREW-IN LEAD, Ser. No. 535,318, filed Sept. 23, 1983, now U.S. Pat. No. 4,570,642. Introducer tools are used to facilitate the introduction and implantation procedure of screw-in leads, such as the introducer tool disclosed in my co-pending application, entitled INTRODUCER TOOL FOR ENDOCARDIAL SCREW-IN LEAD, filed Dec. 19, 1983, Ser. No. 562,830.

Although the introducer tool disclosed in my co-pending application Ser. No. 562,830 has been satisfactory for facilitating the introduction of the lead into a patient, there have been infrequent occasions when the stylet has buckled during the introduction procedure. The buckling of the stylet is attributable to the particular construction of the introducer tool disclosed in my earlier co-pending application Ser. No. 562,380. Although this infrequent buckling does not prevent introduction of the lead, it does interfere with smooth introduction and is annoying to the attending physician.

SUMMARY OF THE INVENTION

It is a general object of this invention to provide an improved introducer tool for a screw-in lead which permits smooth introduction of the lead and stylet, and which locks the stylet to the introducer tool to permit ready fixation by rotation of the lead relative to the introducer tool and stylet.

Another object of this invention is to provide a novel and improved introducer tool for use with both unipolar and bipolar endocardial leads.

A further object of this invention is the provision of an introducer for an endocardial screw-in lead which is locked to the lead during the introduction procedure and which is locked to the stylet during fixation.

These and other objects of the invention will be more fully defined in the following specification.

FIGURES OF THE DRAWING

FIG. 1 is a perspective view of the introducer tool which is designed for a bipolar endocardial lead;

FIG. 2 is a longitudinal sectional view through the tool illustrated in FIG. 1;

FIG. 3 is a cross-sectional view taken approximately along the line 3—3 of FIG. 1 and looking in the direction of the arrows;

FIG. 4 is a cross-sectional view taken approximately along the line 4—4 of FIG. 1 and looking in the direction of the arrows;

FIG. 5 is a cross-sectional view taken approximately along the line 5—5 of FIG. 1 and looking in the direction of the arrows;

FIG. 6 is a cross-sectional view taken approximately along the line 6—6 of FIG. 1 and looking in the direction of the arrows;

FIG. 7 is a cross-sectional view taken approximately along the line 7—7 of FIG. 1 and looking in the direction of the arrows;

FIG. 8 is a cross-sectional view taken approximately along the line 8—8 of FIG. 1 and looking in the direction of the arrows;

DESCRIPTION OF THE PREFERRED EMBODIMENT

Figure 9:
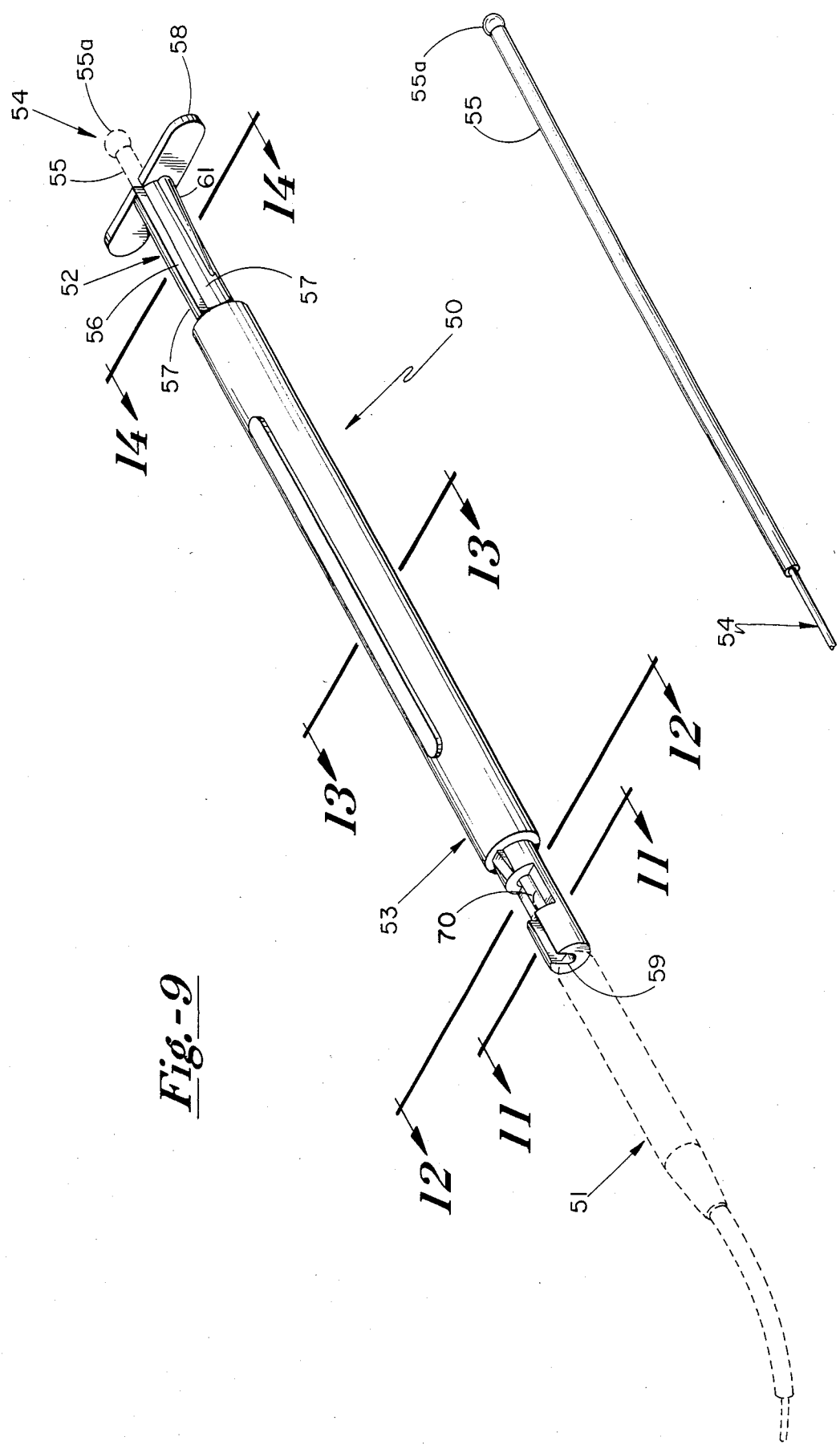
FIG. 9 is a perspective view of a modified form of the introducer tool and is specifically intended for use with a unipolar endocardial screw-in lead.

Referring now to the drawings, and more specifically to FIGS. 1-8, it will be seen that one embodiment of the novel introducer tool, designated generally by the reference numeral 10, is thereshown. The introducer tool 10 is specifically intended for use with a bipolar endocardial screw-in lead 11. In this regard, it is pointed out that the bipolar lead 11 is identical in substantially all respects to the endocardial lead disclosed in my co-pending application, entitled ENDOCARDIAL EXTENDABLE SCREW-IN LEAD, filed Sept. 23, 1983, Ser. No. 535,318, and the disclosure thereof is incorporated herein by reference.

The introduction tool 10 includes an elongate plunger housing 12 which is slidably positioned within an elongate locking tube 13. The plunger housing and locking tube are formed of a suitable moldable plastic material. A stylet 14 is insertable through the lumen or passage in the plunger housing 12 and the stylet is provided with an elongate stylet plunger 15 on its proximal end. The stylet 14 is formed of wire and has proximal and distal ends. The stylet plunger 15 is formed of plastic and terminates in a knob 15a. It will be appreciated that, during the insertion or introduction procedure, the stylet is inserted through the lumen defined by the coil conductors in a well-known manner. The lead 11 is covered with a sleeve or jacket of electrically insulating material; namely, silicon rubber.

Referring now to FIGS. 1 and 2, it will be seen that the plunger housing 12 is of elongate substantially cylindrical configuration and has a length dimension substantially greater than the length dimension of the locking tube 13. The plunger housing 12 has proximal and distal ends, and it will be noted that the proximal end portion has a pair of axially extending diametrically opposed splits 16 therein. These splits 16 define a pair of opposed semi-cylindrical clamping portions 17. The proximal end of the plunger housing terminates in a pair of outwardly projecting finger engaging elements 18.

The distal end portion of the plunger housing has an elongate longitudinally extending lower slit 19 therein and a longitudinally extending elongate upper slit 20 therein. The upper and lower slits 19 are disposed in opposed relation with respect to each other and define a pair of clamping members 21 at the distal end portion of the plunger housing. Each of the clamping members 21 has a front notch 22 therein and a rear notch 23 therein. These notches expose the contacts on the connector pin of the bipolar lead.

Referring now to FIGS. 3–8, it will be seen that the plunger housing 12 has a pair of opposed slide elements 25 integrally formed therewith and projecting outwardly therefrom. It will further be noted that these slide elements 25 engage the inner surface 24 of the locking tube 13. In this regard, it will be noted that the exterior diameter of the plunger housing is spaced radially inwardly, in general, from the inner surface 24 of the locking tube.

Referring again to FIG. 2, it will be seen that the plunger housing 12 is provided with an inclined cam or ramp 26 located at the proximal end of the upper slit 20 in the proximal end portion thereof. The cam or ramp is inclined in a proximal or rearward direction and defines a rearwardly facing stop shoulder 27. It will also be noted that the lumen or opening through the plunger housing 12 is uniform throughout a major portion of its length, but is reduced as at 28 adjacent the clamping members 21. This reduced opening 28 through the plunger housing defines a rearwardly facing annular shoulder 29. In the embodiment shown, the annular shoulder may be engaged by the forward end of the stylet plunger 15 to limit further forward movement of the stylet. It will also be noted that the plunger housing 12 has an elongate longitudinally extending groove 30 therein extending from the shoulder 27 and terminating adjacent, but spaced from the rear or proximal end of the plunger housing. The groove 30 defines a forwardly facing shoulder 31 at its proximal or rear end thereof.

Referring again to FIGS. 1 and 2, it will be seen that the locking tube 13 is of substantially cylindrical configuration and is provided with a notch therein adjacent the proximal end portion thereof. The notch 32 is of semi-cylindrical configuration and exposes the front notch 22 and the rear notch 23 in the plunger housing when the latter is moved forwardly to an advanced position. It will further be noted that the interior diameter 24 through the plunger tube is substantially uniform throughout its length as best seen in FIGS. 3–8.

It will be seen that the locking tube 13 is provided with a guide element 33 integrally formed therewith intermediate the ends thereof and projecting radially inwardly therefrom. The guide element 33 projects into the groove 30 in the plunger housing 12. The guide element 33 is movable in the groove 30 to permit relative longitudinal but non-rotatable movement between the plunger housing and the locking tube 13. It is pointed out that, when the locking tube is assembled with the plunger housing, the guide element is cammed over the ramp 26 into the groove 30 to permanently interlock the locking tube and plunger housing together. It will also be noted that the exterior surface of the locking tube has a pair of elongate longitudinally extending embossed portions 34 integrally formed therewith on opposed portions thereof.

In use, the connector pin 35 of the lead 11 will be inserted between the clamping members 21 at the proximal end of the plunger housing. The plunger housing 12 will be retracted to the position illustrated in FIG. 1 so that the locking tube 13 is in substantially concentric relation around the proximal end portions of the plunger housing. When the plunger housing and locking tube are in this position, the locking tube 13 causes the clamping members 21 to be clamped against the connector pin 35 and the stylet will be inserted through the plunger housing and into the lumen of the conductor coil until the stylet engages the helix assembly located in the hollow electrode at the distal end portion of the lead.

After the lead has been passed through the superior vena cava vein into the right atrium, or into the right ventricle, the physician will monitor the area by connecting the oscilloscope or other monitoring device between the connector pin on the lead and ground. Again, it will be appreciated that a suitable electrical clip may be applied to those portions of the bipolar connector pin positioned within the front notch 22 and the rear notch 23. Once an acceptable position for an attachment is found, the stylet plunger 15 will be urged into the lead a distance of approximately 2 or 3 inches, which causes the helix assembly to be shifted longitudinally of the electrode barrel until the helix assembly reaches a fully extended position. This procedure is set forth in detail in co-pending application Ser. No. 535,318, and reference is made to this application for a description of the procedure.

After the helix assembly has been moved to the extended position, the physician may then release the stylet so that any tension in the lead will permit the stylet to retract relative to the plunger housing. Thereafter, the physician will engage the finger engaging elements 18 in the same manner one would engage and shift a syringe plunger to thereby shift the stylet plunger 15 in an advanced direction. When this occurs, the locking tube 13 will cause the clamping portion 17 at the proximal end portion of the plunger housing 12 to be clamped against the stylet plunger 15 and to lock the stylet against movement relative to the plunger housing. Further, when the plunger housing is advanced, the clamping members 21, which have been clamped against the connector pin 35, will be released from clamping relation with the connector pin to permit rotation of the lead.

The physician may then grip the introducer tool and the proximal end of the lead with one hand and rotate the lead with the thumb and forefinger about the stylet in a clockwise direction approximately six turns to engage the endocardium with the corkscrew helical element of the helix assembly. The stylet 14 will then be retracted an additional three or four inches and a slight tension will thereafter be applied to the lead to verify the fixation with the fluoroscopy unit. After verification of fixation, the stylet may then be removed from the lead and the introducer tool will be disengaged and removed from the connector lead.

Referring now to FIGS. 9–14, it will be seen that a different embodiment of the introducer tool, designated generally by the reference numeral 50 is thereshown. The introducer tool illustrated in FIGS. 9–14 is similar in most respects to the embodiment of FIGS. 1–9, but this introducer tool is intended for use with a unipolar lead 51, rather than a bipolar lead. The introducer tool 50 includes a plunger housing 52 which is slidably positioned within a locking tube 53. An elongate stylet 54 is provided, having an elongate stylet plunger 55 at its proximal end. The stylet 54 is formed of wire and is inserted through the plunger housing and into the lumen of the lead 51 in the manner of the embodiment of FIG. 1. The stylet plunger is formed of plastic and is provided with a knob 55a at its proximal end.

Figure 10:
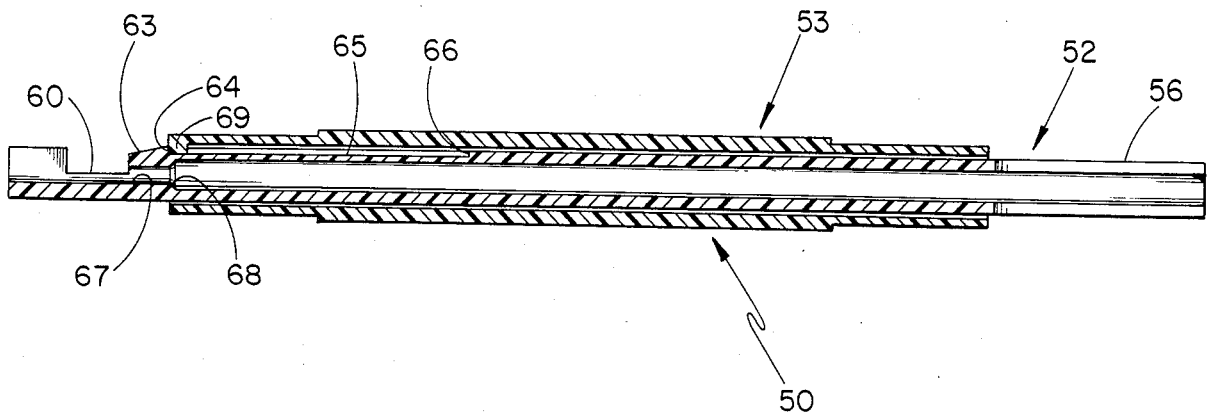
FIG. 10 is a longitudinal sectional view through the lead illustrated in FIG. 9.
Figure 11:
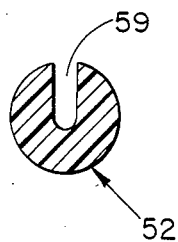
FIG. 11 is a cross-sectional view taken approximately along the line 11—11 of FIG. 9 and looking in the direction of the arrows.
Figure 12:
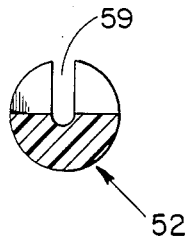
FIG. 12 is a cross-sectional view taken approximately along the line 12—12 of FIG. 9 and looking in the direction of the arrows.
Figure 13:
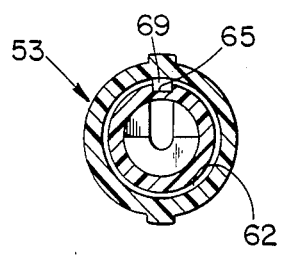
FIG. 13 is a cross-sectional view taken approximately along the line 13—13 of FIG. 9 and looking in the direction of the arrows.

The plunger housing and locking tube are also formed of a suitable moldable plastic and it will be noted that the plunger housing is of elongate generally cylindrical configuration. Referring now to FIGS. 9 and 10, it will be seen that the plunger housing is provided with a pair of elongate longitudinally extending, opposed splits 56 extending from the proximal end thereof to define a pair of generally semi-cylindrical clamping portions 57. Each clamping portion 57 terminates in a finger engaging element 58 which projects substantially radially therefrom.

Figure 14:
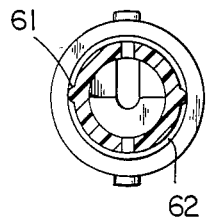
FIG. 14 is a cross-sectional view taken approximately along the line 14—14 of FIG. 9 and looking in the direction of the arrows.

Referring now to FIGS. 9–12, it will be seen that the distal end portion of the plunger housing 52 has an elongate longitudinally extending slit 59 therein which communicates with the opening through the plunger housing. The connector pin of the lead 51 is insertable into the distal end of the plunger housing 52. The distal end portion of the plunger housing 52 also has a semi-cylindrical notch 60 therein which serves to expose the conductive surface of the connector pin when the connector pin is inserted into the distal end portion of the plunger housing. Referring now to FIGS. 9 and 14, it will be seen that the exterior surface of the plunger housing 52 is provided with a pair of cam elements 61 which extend from the finger engaging elements 58 longitudinally or axially and gradually taper in a distal direction into the cylindrical surface of the plunger housing. These cam elements 61 permit the clamping portions 57 to be progressively clamped into clamped relation with the stylet plunger 55 to lock the stylet against movement relative to the plunger housing during fixation of the lead to the endocardium. The cam elements 61 are engaged by the inner surface 62 of the locking tube when the plunger housing is shifted to the advanced position in the locking tube 53.

Referring again to FIGS. 9 and 10, it will be seen that the plunger housing 53 is provided with a cam or ramp 63 adjacent the notch 60 at the proximal end portion of the plunger housing. The cam or ramp 63 is inclined rearwardly or in a proximal direction and defines a rearwardly facing shoulder 64. The plunger housing is also provided with an elongate longitudinally extending groove 65 in the exterior surface thereof which terminates distally at the shoulder 64. Groove 65 also terminates rearwardly or in a proximal direction at the rear shoulder 66.

The opening or lumen through the plunger housing 62 is of substantially uniform diameter, but is reduced adjacent its distal end portion, as at 67. This reduced opening 67 defines a rearwardly facing annular shoulder 68, which may be engaged by the forward portion of the stylet plunger 55 to limit further advancement of the stylet relative to the plunger housing. It will also be noted that the locking tube 53 is provided with an inwardly projecting guide element 69 at its distal end which is positioned in the groove 65. With this arrangement, the guide element 69 permits longitudinal, but non-rotative movement of the plunger housing 52 relative to the locking tube 53. The extent of movement of the plunger housing relative to the locking tube is determined by the length of the groove 65. In the embodiment shown, it will be noted that the locking tube is not disposed around the distal end portion of the plunger housing when the plunger housing is in the advanced position. However, the locking tube 53 will engage the finger engaging elements 58 on the plunger housing 52 when the plunger housing is in the advanced position.

The introducer tool 50 will be used in substantially the same manner as the embodiment of FIGS. 1–8. In this regard, a connector pin 70 of the lead 51 will be inserted into the distal end of the plunger housing so that a portion of the connector pin will be exposed by the notch 60 for an electrical connection in the manner of the embodiment of FIG. 1. It is pointed out that the distal end portion of the housing 52 frictionally engages the connector pin and does not require the locking tube to assist in the clamping function in the manner of the embodiment of FIG. 1.

The plunger housing 52 will be in the retracted position during the introduction of the lead into the atrium or ventricle and the same procedure will be followed as that described with respect to the embodiment of FIG. 1. Again, it is pointed out that, after an acceptable position for attachment is found, the stylet will be urged into the lead to cause the helix assembly to be shifted longitudinally of the electrode barrel until the helix assembly reaches a fully extended position. Monitoring by the physician will permit the physician to observe this condition.

After the helix assembly has reached the extended position, the stylet may be released to permit the stylet to retract in response to any tension therein. The plunger housing 52 will then be advanced so that the clamping portions 57 are clamped against the stylet plunger to lock the stylet against movement relative to the plunger housing. The physician will then rotate the proximal end of the lead relative to the plunger housing and about the stylet to cause the corkscrew helical element to engage the endocardium. After verification of fixation, the stylet may then be removed from the lead and the introducer tool will be disengaged and removed from the connector lead.

Although the particular kind of pacing lead has not been described in this application, it is pointed out that the introducer tool may be readily used with an in-line unipolar, as well as a bipolar, lead in either heart chamber.

In the present embodiment, it will be noted that the introducer tool is positively connected to the lead during the insertion procedure, but then is operable to lock the stylet against movement but permit rotation of the lead relative to the introducer tool about the stylet. It will further be noted that the proximal end portion of the stylet is completely contained within the plunger housing and thereby precludes buckling of the stylet during introduction and fixation of the lead.

Thus, it will be seen that I have provided a novel introducer tool for a screw-in type lead, which is not only of simple and inexpensive construction, but one which functions in a more efficient manner than any heretofore known comparable introducer tool.

What is claimed is:

1. In combination with an intravascular lead including an electrically insulated elongate flexible coil conductor having a lumen therethrough and having proximal and distal ends, a connector element electrically connected to the proximal end of the conductor and a hollow electrode electrically connected to the distal end of the conductor and adapted to contact body tissue, a helix assembly in the electrode being shiftable from a retracted position to an extended position wherein the helix assembly projects outwardly of the electrode, an introducer tool comprising an elongate hollow plunger housing having proximal and distal ends, the distal end of said plunger housing engaging the connector element to secure the latter to the plunger housing, an elongate locking tube positioned around said plunger housing and having proximal and distal ends, cooperating means on said locking tube and plunger housing permitting longitudinal but non-rotatable shifting movement of said plunger housing in said locking tube between retracted and advanced positions, and an elongate stylet having proximal and distal ends and being insertable through the plunger housing and lumen of the conductor for engagement with the helix assembly for non-rotatably shifting the same in a longitudinal direction from the retracted position to the extended position when the plunger housing is in the retracted position, cooperating means on the proximal end of said plunger housing and the proximal end of said stylet to lock the stylet against movement relative to plunger housing when the latter is in the advanced position, whereby the lead may be rotated relative to the plunger housing and about said stylet to permit the helix assembly to penetrate the cardiac tissue and urge the electrode into positive engagement with the tissue.

2. The invention as defined in claim 1 wherein said plunger housing and said locking tube are each of substantially cylindrical configuration.

3. The invention as defined in claim 2 and a notch in said plunger housing adjacent the distal end thereof permitting electrical connection with the connector element.

4. The invention as defined in claim 1 wherein the proximal end portion of the plunger housing has opposed splits therein to define clamping elements thereat, said clamping elements engaging and clamping the proximal end portion of the stylet when said plunger housing is in the advanced position to thereby lock the stylet against movement relative to the plunger housing.

5. The invention as defined in claim 4 and a plurality of camming elements on said clamping elements engaging said locking tube to cam the clamping elements into clamping relation with the stylet when the plunger housing is shifted to the advanced position.

6. The invention as defined in claim 4 and a pair of finger engaging elements, each being integral with one of said clamping elements and projecting outwardly therefrom, said finger engaging elements facilitating movement of said plunger housing between advanced and retracted positions.

7. The invention as defined in claim 1 wherein said cooperating means on said plunger housing and locking tube comprises an elongate guideway on said plunger housing and a guide element on said locking tube projecting into said guideway.

8. The invention as defined in claim 1 wherein the distal end portion of said plunger housing has opposed splits therein to define a pair of clamping elements thereat, said locking tube engaging the distal end portion of said plunger housing when the latter is in the retracted position causing said clamping elements to clamp the connector element of the lead.

* * * * *